United States Patent [19]

Remmen

[11] Patent Number: 5,012,799
[45] Date of Patent: May 7, 1991

[54] INGROWN CORRECTING TOE NAIL APPLIANCE

[76] Inventor: Werner G. Remmen, 6957 Hwy. 10 NW., Anoka, Minn. 55303

[21] Appl. No.: 533,110
[22] Filed: Jun. 4, 1990
[51] Int. Cl.$^5$ .............................................. A61F 5/11
[52] U.S. Cl. .................................................. 128/81 A
[58] Field of Search ..................................... 128/81 A

[56] References Cited

U.S. PATENT DOCUMENTS

| | | | |
|---|---|---|---|
| 132,872 | 11/1872 | Stedman . | |
| 137,106 | 3/1873 | Stedman | 128/81 A |
| 1,213,673 | 1/1917 | Marvel . | |
| 1,451,311 | 4/1923 | Smith . | |
| 2,024,412 | 12/1935 | Wilson | 128/81 |
| 2,405,547 | 8/1946 | Armagost | 128/81 |
| 2,505,086 | 2/1946 | Andrews | 128/81 A |
| 2,567,601 | 9/1951 | Heinold et al. | 128/81 |
| 2,613,667 | 10/1952 | Stanley | 128/81 |
| 2,632,441 | 3/1953 | Tuve | 128/81 |
| 3,032,032 | 5/1962 | Gifford | 128/81 |

FOREIGN PATENT DOCUMENTS

| | | | |
|---|---|---|---|
| 0027425 | of 1896 | United Kingdom | 128/81 A |
| 0791799 | 3/1958 | United Kingdom | 128/81 A |

Primary Examiner—Richard J. Apley
Assistant Examiner—L. Thomas
Attorney, Agent, or Firm—Leo Gregory

[57] ABSTRACT

A spring wire toe nail correcting appliance having a central inverted V-shaped bridge portion have a pair of laterally extending arms having reversely downwardly curved tip portions, the arms defining a transverse curvature less than that of a toe nail, the tip of the V-shaped bridge engaging the nail to exert leverage when the tip portions engage the corners of the toe nail causing said corners to become uplifted.

1 Claim, 1 Drawing Sheet

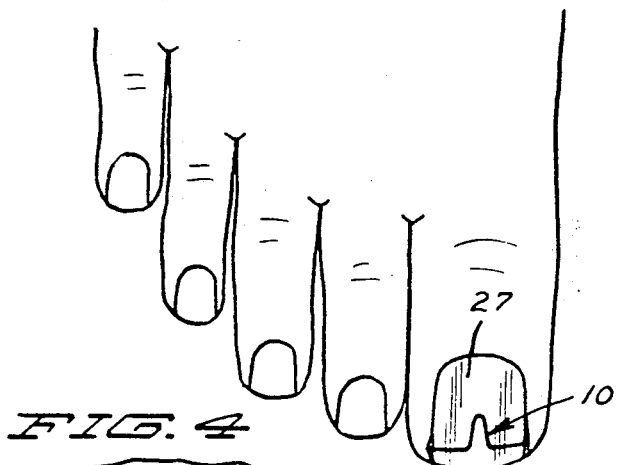
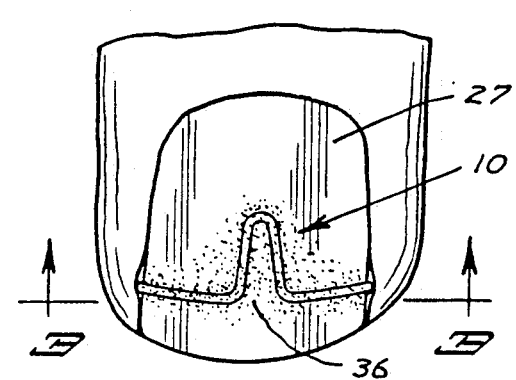
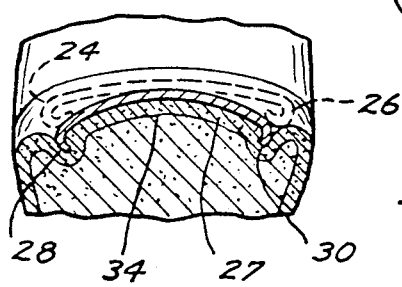
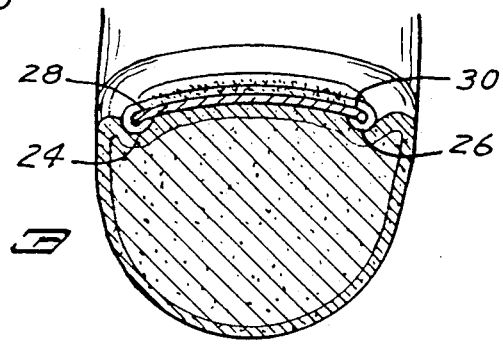
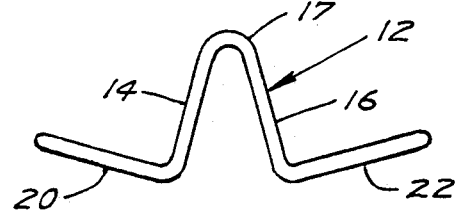
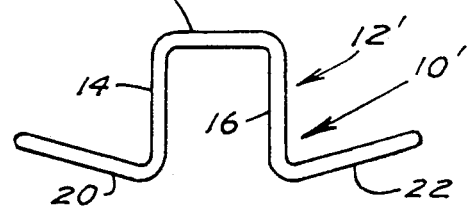
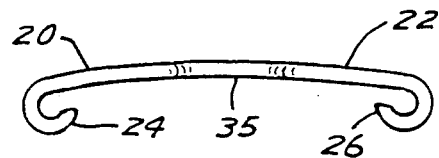
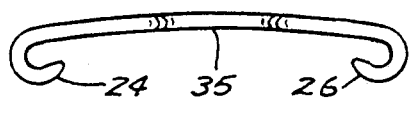
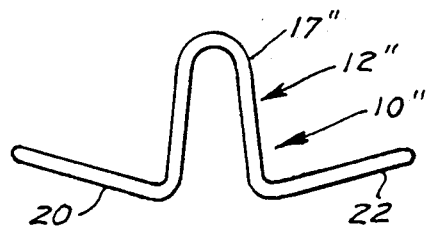
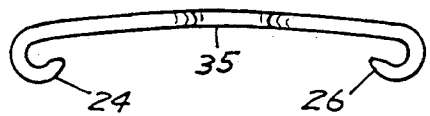

INGROWN CORRECTING TOE NAIL APPLIANCE

BACKGROUND OF INVENTION

1. Field of Invention

This invention relates to an appliance to correct an ingrown toe nail.

2. Description of the Previous Art

Over the years considerable effort has been directed to the making and improvement of appliances to correct ingrown toe nails.

Correction is accomplished by applying to a toe nail an appliance which extends thereacross and has under curved tip portions forming hooks to engage the underside of the corner portions of a toe nail and exert an upward force to cause the nail to grow straight outwardly in a naturally correct position.

The following are representatives of prior art patents disclosing various related appliances.

E. E. Stedman in his 1872 U.S. Pat. No. 132,872 discloses and arcuate spring which overlies a toe nail engaging the corners thereof and apply an uplifting force. The spring has to be of a length to fit the nail.

T. L. Marvel in his U.S. Pat. No. 1,213,673 shows a spring member engaging the corners of a toe nail having a reversely curved member extending thereacross exerting a lifting force. This member must be of a length to fit the nail.

G. W. Smith in his 1923 U.S. Pat. No. 1,451,311 shows an extensible device formed of a pair of flat overlapping resilient members deformed to exert an upward force on the corners of a toe nail.

H. S. Armagost in his 1946 U.S. Pat. No. 2,405,547 shows a substantially U-shaped wire having looped ends to engage the corners of a toe nail, the loops being adapted to having end portions dig into the nail for anchorage.

V. A. Gifford in his U.S. Pat. No. 3,032,032 shows a serpentine wire spring to adjustably extend across a toe nail and engage the corners thereof.

SUMMARY OF THE INVENTION

It is desirable and an object of this invention to have an appliance to correct an ingrown toe nail, the device consisting of a single piece of surgical or stainless steel spring wire construction being variable in width to accommodate the width of a toe nail, to self-generate the requisite lifting pressure to be exerted upon a toe nail to cause a correction of the ingrown condition to occur and in being applied to a toe nail to be caused to lie flat upon the nail.

These and other objects and advantages of the invention will be set forth in the following description made in connection with the accompanying drawings in which like reference characters refer to similar parts throughout the several views.

BRIEF DESCRIPTION OF THE DRAWINGS

FIG. 1 is a plan view of the forepart of a foot showing the appliance comprising the invention herein in operating position;

FIG. 2 is an enlarged view in plan showing one toe have the appliance positioned thereon;

FIG. 3 is an enlarged view in cross-section taken on line 3—3 of FIG. 2;

FIG. 4 is a view similar to FIG. 4 showing the invention herein in partially applied position;

FIG. 5 is a plan view of the invention herein as shown in FIG. 2;

FIG. 6 is a view in front elevation of the invention as shown in FIG. 5;

FIG. 7 is a view similar to that of FIG. 5 showing a modification thereof;

FIG. 8 is a view of the modification of FIG. 7 in front elevation;

FIG. 9 is a view similar to that of FIG. 5 showing another modification thereof; and FIG. 10 is a view in front elevation of the modification of FIG. 9.

DESCRIPTION OF A PREFERRED EMBODIMENT

Referring to the drawings, the invention herein comprising an appliance to correct an ingrown toe nail is indicated generally by the reference numeral 10.

The appliance is formed preferably of a surgical or stainless steel wire such as 304 wire material on the order of 0.046 inches in diameter having a central inverted V-shaped bridge or span portion 12. Said appliance in the embodiment here presented in FIGS. 1–5 is shown with said central inverted V-shaped portion comprising side members 14 and 16 converging and joining at an apex 17

Respectively extending laterally of the free ends of said side members 14 and 16 are arm members or arms 20 and 22 of which the outer ends are reversely curved downwardly to form small hook portions 24 and 26 to be slipped over the side edge portion of a toe nail 27 to engage and receive therein the corner portions 28 and 30 of the toe nail which for purposes herein will be the large toe nail.

Said arms 20-22 define a transverse curvature 35 which is less than the transverse or cross-sectional curvature 34 of said toe nail 27, to which the appliance is to be applied. Said large toe nail 27 is a representative large toe nail.

The appliance is made preferably of surgical steel or stainless steel to be resistant to deterioration which may be caused by the emissions of any body chemicals or acids. The appliance is well polished and has no sharp edges or corners.

The bridge portion 12 of the appliance makes it possible for the appliance to be adjustable to accomodate the width of any particular toe nail and provided, as will be described, is the requisite torque to cause each of said hook portions engaging the corners of the toe nail to urge the corners upwardly to cause the nail to grow outwardly forwardly in a correct natural position.

In being applied, the width of the appliance will be adjusted or extended to be substantially the width of the toe nail as indicated in FIG. 4. The hook portions 24 and 26 will be positioned to receive therein the nail corners 28 and 30 such as by being drawn on over the end of the nail or pressed downwardly over the side edge thereof. The transverse curvature of the appliance being less than that of the toe nail, the tip of said span portion of the appliance will engage the midpoint surface area of the nail and the ends or hook portions 24 and 26 of the arms are pulled downwardly to cause the arms to correspond to the curvature of the toe nail as indicated in FIG. 3 and this bending action of the arms applies a torque to the sides 14 and 16 which causes the hook portions to be under a constant lifting force. It is this lifting force which causes the corners of the toe nail to become raised sufficiently to straighten upwardly the corners of the nail and cause them to grow straight outwardly in a correct position. Thus the ingrowing tendency of the nail is overcome and the ingrown condition becomes corrected.

The application of the appliance requires no particular expertise. All that is required for a successful installation is a careful following of the description as given for the application of the appliance.

Referring to FIGS. 7,8 and 9,10, modifications are shown of the embodiment of the appliance above described and in which similar parts are indicated by the same reference numerals and the modified portions are indicated by the same reference numerals with a prime or double prime added.

Thus in FIGS. 7 and 8, the modification 10' is shown having a substantially U-shaped bridge portion 12' having a flat top portion 17' and in all other respects the appliance is as above described in structure and function.

In FIGS. 9 and 10, the modification 10" is shown in which the bridge portion has 12" a curved apex 17" and in all other respects the appliance is as above described in structure and appearance.

This appliance has proved to be very successful in effecting the correction indicated in a very simple and painless manner. The appliance may bear an ornament for use bare foot as with sandals or other toe-less foot wear.

In order to prevent the appliance from becoming dislodged such as in the course of putting on hose, a soluble liquid adhesive indicated at 36 is applied, such as a nail polish, and the same is readily removed such as with a nail polish remover.

It will of course be understood that various changes may be made in form, details, arrangement and proportions of the product without departing from the scope of the invention which, generally stated, consists in a product capable of carrying out the objects above set forth, in the parts and combination of parts disclosed and defined in the appended claims.

What is claimed is:

1. An appliance correcting an ingrown toe nail, comprising
   a resilient member of narrow width comprising
   a central inverted V-shaped span portion of said member forming a pointed tip,
   said span portion having side members joined at one end thereof forming said tip,
   an arm extending from the free end of each of said side members,
   said arms being disposed laterally in opposed relation to one another defining a transverse curvature thereacross which is a lesser curvature than the transverse curvature of a toe nail to which said appliance is applied,
   a downwardly reversely curved tip portion forming a hook at the end of each of said arms,
   said reversely curved tip portions being pressed downwardly to receive the corners of said toe nail causing the tip of said inverted V-shaped span portion to engage the surface of said toe nail leveraging said arms to develop a torque on the longitudinal axes of said side members, and
   said torque urging said hooks upwardly elevating the corners of said toe nail sufficiently to cause said toe nail to grow out in a naturally correct position.

* * * * *